(12) United States Patent
Tawada et al.

(10) Patent No.: US 7,354,153 B2
(45) Date of Patent: Apr. 8, 2008

(54) FUNDUS CAMERA

(75) Inventors: Akira Tawada, Gamagori (JP); Setsuo Saito, Aichi-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 362 days.

(21) Appl. No.: 11/063,840

(22) Filed: Feb. 23, 2005

(65) Prior Publication Data

US 2005/0225722 A1 Oct. 13, 2005

(30) Foreign Application Priority Data

Feb. 27, 2004 (JP) ............................. 2004-054895
Feb. 16, 2005 (JP) ............................. 2005-039885

(51) Int. Cl.
*A61B 3/14* (2006.01)

(52) U.S. Cl. ...................... 351/206; 351/205; 351/207; 351/213

(58) Field of Classification Search ................ 351/205, 351/206, 207, 213; 396/11
See application file for complete search history.

(56) References Cited

U.S. PATENT DOCUMENTS 4,098,549 A 7/1978 Matsumura

2004/0169818 A1 * 9/2004 Hoshino .................... 351/205
2004/0252276 A1 12/2004 Nanjo et al.

FOREIGN PATENT DOCUMENTS

| JP | 60-57852 | 12/1985 |
| JP | 04295332 A | * 10/1992 |
| JP | A 2003-225208 | 8/2003 |
| JP | A 2004-261293 | 9/2004 |

* cited by examiner

*Primary Examiner*—Scott J. Sugarman
*Assistant Examiner*—James R Greece
(74) *Attorney, Agent, or Firm*—Oliff & Berridge, PLC

(57) ABSTRACT

A fundus camera capable of favorably obtaining a photographed fundus image and an observation fundus image, has an optical system having an objective lens and a diaphragm at a conjugate position with a pupil relative to the lens, for performing visible photographing and infrared observation via the lens and an aperture of the diaphragm, an optical system for illumination with visible and infrared light via the lens, a first plate, with a first black dot to cover an aperture image and at a conjugate position on an optical path with a position where a virtual image is formed relative to a lens surface reflecting the visible light, and a second plate, with a second black dot to cover an aperture image and in the vicinity of a conjugate position on the path with a position where a virtual image is formed relative to the surface reflecting the infrared light.

2 Claims, 8 Drawing Sheets

US 7,354,153 B2

FUNDUS CAMERA

BACKGROUND OF THE INVENTION

1. Field of the Invention

The present invention relates to a fundus camera for photographing a fundus of an eye of an examinee.

2. Description of Related Art

Conventionally, there is known a fundus camera of non-mydriasis type which is provided with an observation/photographing optical system for performing infrared observation and visible photographing of a fundus via an objective lens and an aperture of a diaphragm, and an illumination optical system for illuminating the fundus with infrared light for observation and visible light for photographing via the objective lens. In this type of fundus camera, the objective lens is shared by the observation/photographing optical system and the illumination optical system; therefore, the visible light for photographing is reflected by the objective lens inadvertently to pass through the aperture of the diaphragm, causing a flare, a ghost and the like at the time of photographing. Accordingly, a black-dot plate is arranged on an optical path of the illumination optical system to prevent the passing of the visible light for photographing. However, this black-dot plate is arranged specifically for the visible light for photographing; therefore, due to the difference in wavelengths between visible light and infrared light, the infrared light for observation is reflected by the objective lens and cannot be prevented from passing through the aperture of the diaphragm. In order to observe the fundus favorably, the passing of the infrared light for observation should also be prevented.

SUMMARY OF THE INVENTION

An object of the invention is to overcome the problems described above and to provide a fundus camera capable of obtaining a favorable photographed image of a fundus and a favorable observation image of the fundus.

To achieve the objects and in accordance with the purpose of the present invention, a fundus camera has a photographing/observation optical system having an objective lens and a diaphragm arranged at a conjugate position with a pupil of the eye in relation to the objective lens, for performing visible photographing and infrared observation of the fundus via the objective lens and an aperture of the diaphragm, an illumination optical system for illuminating the fundus with visible light for photographing and infrared light for observation via the objective lens, a first black-dot plate, provided with a first black dot in a size to cover an image of the aperture of the diaphragm and arranged at a position on an optical path of the illumination optical system, the position conjugate with a position at which a virtual image of the aperture of the diaphragm is formed in relation to a reflection surface in a case where the visible light for photographing is reflected by the objective lens, and a second black-dot plate, provided with a second black dot in a size to cover an image of the aperture of the diaphragm and arranged in the vicinity of a position on the optical path of the illumination optical system, the position conjugate with a position at which a virtual image of the aperture of the diaphragm is formed in relation to the reflection surface in a case where the infrared light for observation is reflected by the objective lens.

In another aspect of the present invention, a fundus camera has an objective lens, a first illumination optical system for illuminating the fundus with visible light for photographing via the objective lens, a second illumination optical system for illuminating the fundus with infrared light for observation via the objective lens, a photographing optical system having a diaphragm arranged at a conjugate position with a pupil of the eye in relation to the objective lens and a first image-pickup element, for photo-receiving the visible light reflected from the fundus via the objective lens and an aperture of the diaphragm by using the first image-pickup element to perform visible photographing of the fundus, an observation optical system having a second image-pickup element, for photo-receiving the infrared light reflected from the fundus via the objective lens and the aperture of the diaphragm to perform infrared observation of the fundus, a first black-dot plate, provided with a first black dot in a size to cover an image of the aperture of the diaphragm and arranged at a position on an optical path of the first illumination optical system, the position conjugate with a position at which a virtual image of the aperture of the diaphragm is formed in relation to a reflection surface in a case where the visible light for photographing is reflected by the objective lens, and a second black-dot plate, provided with a second black dot in a size to cover an image of the aperture of the diaphragm and arranged in the vicinity of a position on the optical path of the second illumination optical system, the position conjugate with a position at which a virtual image of the aperture of the diaphragm is formed in relation to the reflection surface in a case where the infrared light for observation is reflected by the objective lens.

Additional objects and advantages of the invention are set forth in the description which follows, are obvious from the description, or may be learned by practicing the invention. The objects and advantages of the invention may be realized and attained by a fundus camera in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
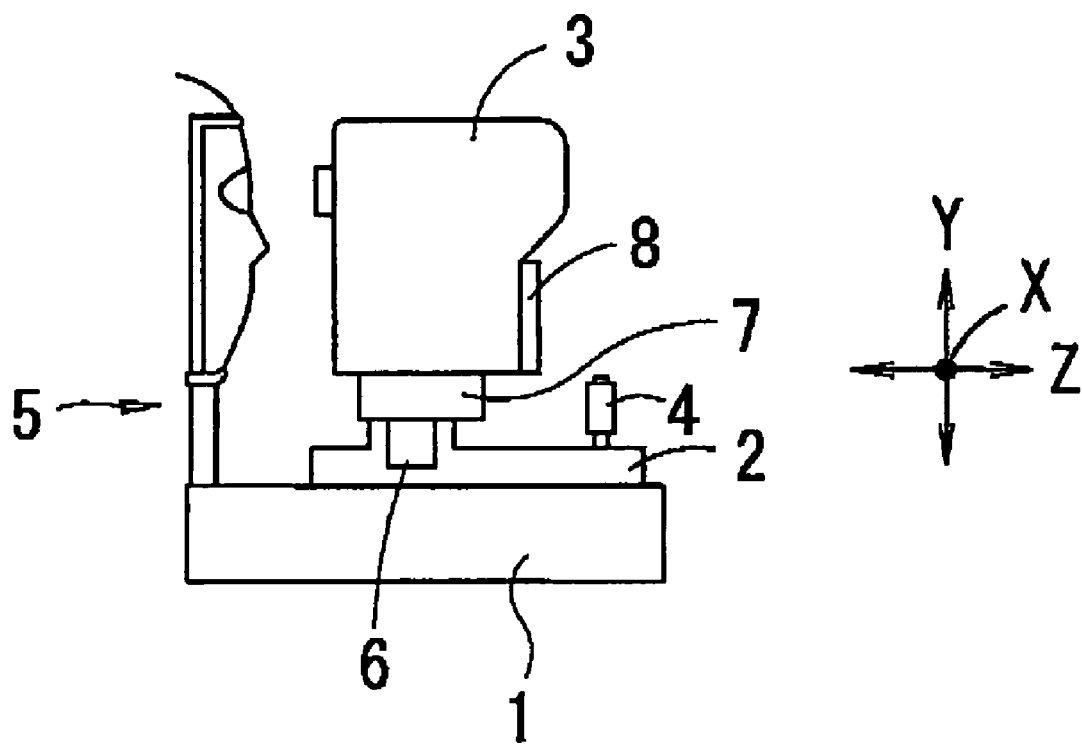
FIG. 1 is a view showing a schematic configuration of a fundus camera.

A detailed description of one preferred embodiment of a fundus camera embodied by the present invention is provided below with reference to the accompanying drawings. FIG. 1 is a view showing a schematic configuration of a fundus camera of non-mydriasis type consistent with the preferred embodiment of the present invention.

The fundus camera is provided with a base 1, a mobile base 2 movable in a right/left direction (hereinafter referred to as an "X-direction") and a back/forth direction (hereinafter referred to as a "Z-direction") with reference to the base 1 through tilting operation of a joystick 4, a photographing part 3 movable in the right/left direction, an up/down direction (hereinafter referred to as a "Y-direction") and the back/forth direction with reference to the mobile base 2 under the control of a control part 81 described later, and a face support unit 5 fixedly arranged on the base 1 for supporting a face (a head) of an examinee. An X- and Z-moving mechanism part 7 moves the photographing part 3 in the X- and Z-directions under the control of the control part 81. A Y-moving mechanism part 6 moves the photographing part 3 in the Y-direction under the control of the control part 81. Besides, for this kind of three-dimensional moving mechanism, a known mechanism may be employed. Further, the photographing part 3 is also moved in the Y-direction by actuating the Y-moving mechanism part 6 through rotational operation of the joystick 4. A monitor 8 for displaying an observation image and a photographed image is provided on an examiner's side of the photographing part 3.

Figure 2:
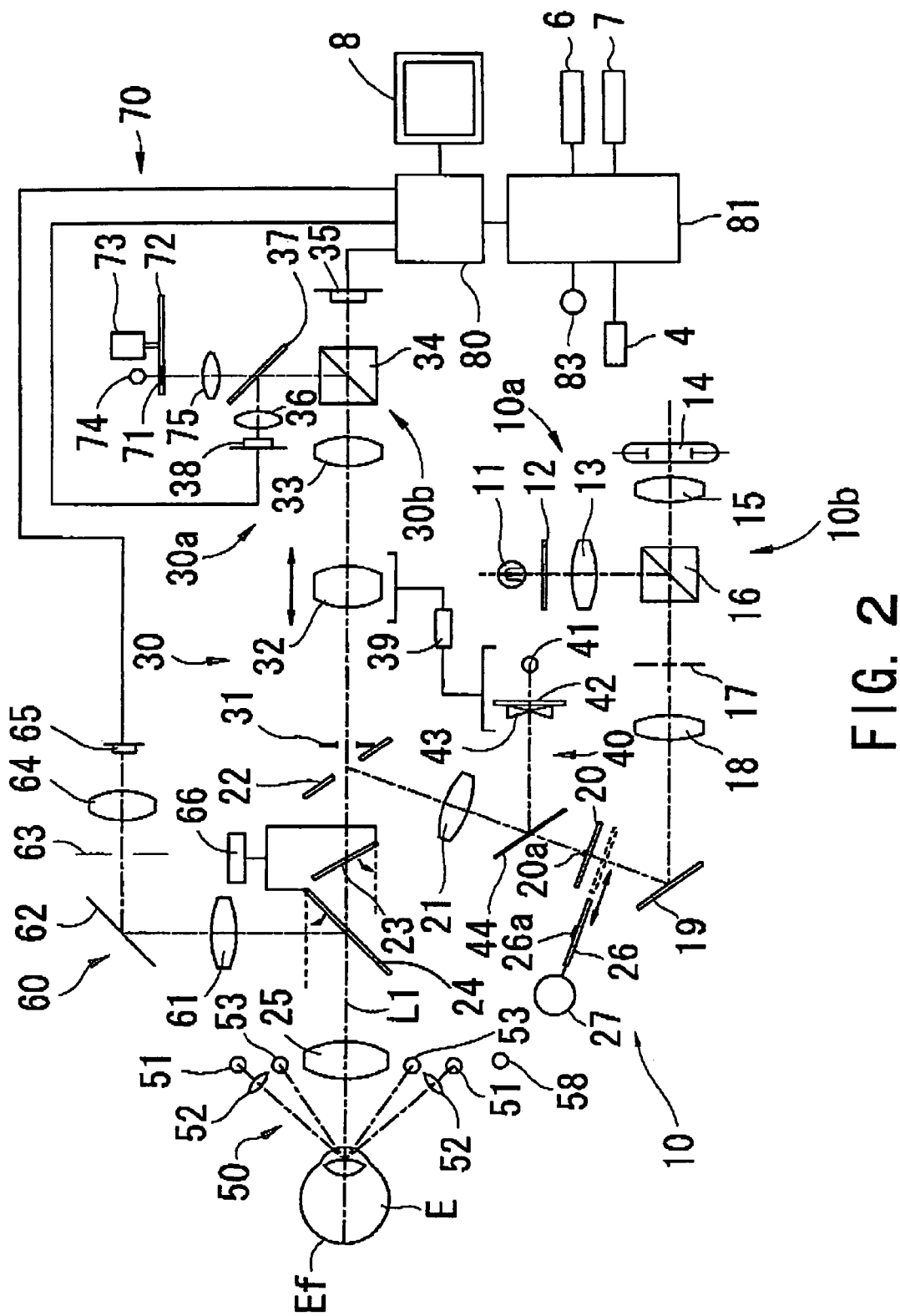
FIG. 2 is a view showing a schematic configuration of an optical system and a control system of the fundus camera.

FIG. 2 is a view showing a schematic configuration of an optical system and a control system housed in the photographing part 3. The optical system generally consists of an illumination optical system 10, a fundus observation/photographing optical system 30, a focus target projection optical system 40, an alignment target projection optical system 50, an anterior-segment observation optical system 60, and a fixation target presenting optical system 70.

<Illumination Optical System 10>

The illumination optical system 10 includes an illumination optical system 10a for fundus observation and an illumination optical system 10b for photographing. Infrared to visible illumination light emitted from an illumination light source 11 for fundus observation such as a halogen light is made into infrared illumination light by an infrared transmission filter 12 which transmits light within an infrared wavelength range of approximately 750 nm to approximately 880 nm, and reflected by a dichroic mirror 16 via a condenser lens 13. The dichroic mirror 16 has a wavelength-selecting property of reflecting approximately all light in the infrared wavelength range and transmitting approximately all light in a visible wavelength range. The infrared illumination light reflected by the dichroic mirror 16 passes through a slit plate 17 and a relay lens 18 and is reflected by a reflection mirror 19, and further passes through a black-dot plate 20 having a black dot 20a at its center, a half mirror 44 and a relay lens 21 and is reflected by a peripheral part of an aperture of an apertured mirror 22 to be projected onto a fundus Ef of an eye E of the examinee via a biconvex objective lens 25. The slit plate 17 has a ring-slit aperture about its center part (i.e., about an optical axis). Besides, an infrared light source such as an infrared light-emitting diode may be used instead of the light source 11 such as the halogen light and the filter 12.

Visible illumination light emitted from a visible illumination light source 14 for photographing such as a flash light passes through a condenser lens 15 and is transmitted through the dichroic mirror 16 to be projected onto the fundus Ef via the slit plate 17 to the objective lens 25.

In addition, arranged on an optical path between the mirror 19 and the black-dot plate 20 is a movable black-dot plate 26 having a black dot 26a at its center. The black-dot plate 26 is inserted into an optical path of the illumination optical system 10 by an inserting/removing mechanism part 27 constituted of a solenoid and the like at the time of fundus observation and is removed therefrom at the time of fundus photographing.

<Fundus Observation/Photographing Optical System 30>

The fundus observation/photographing optical system 30 includes a fundus observation optical system 30a and a photographing optical system 30b. The infrared light and the visible light reflected from the fundus Ef pass through the objective lens 25, the aperture of the apertured mirror 22, an aperture of a diaphragm 31 arranged in the vicinity of the aperture of the apertured mirror 22, a focusing lens 32, and an image forming lens 33, to enter a dichroic mirror 34. The diaphragm 31 (its aperture) is arranged in a position approximately conjugate with a pupil of the eye E in relation to the objective lens 25. The focusing lens 32 is arranged movably by a moving mechanism part 39 consisting of a motor and the like, in a direction of an optical axis L1 of the fundus observation/photographing optical system 30 (i.e., an optical axis of the objective lens 25). The dichroic mirror 34 has a wavelength-selecting property of reflecting approximately all light in the infrared wavelength range, and reflecting a part (a small proportion) of light in the visible wavelength range and transmitting the other part (a large proportion). The visible reflection light transmitted through the dichroic mirror 34 is photo-received on a CCD camera 35 for photographing having sensitivity to the visible wavelength range to form an image of the fundus Ef. Also, the infrared reflection light reflected by the dichroic mirror 34 is reflected by a dichroic mirror 37, and photo-received on a CCD camera 38 for fundus observation having sensitivity to the infrared wavelength range via a relay lens 36, to form an image of the fundus Ef. The dichroic mirror 37 has a wavelength-selecting property of reflecting approximately all light in the infrared wavelength range and transmitting approximately all light in the visible wavelength range. Besides, the CCD camera 38 doubles as image-pickup means for focus target detection to be described later (i.e., the fundus observation optical system 30a doubles as a focus target detection optical system), and picks up the image of the fundus Ef formed by the light source 11 and an image of a focus target formed by the focus target projection optical system 40 to be described later. Incidentally, while it is advantageous to use focus target detection means doubling as fundus image pickup means as in the present embodiment, a dedicated one may be arranged.

Figure 3:
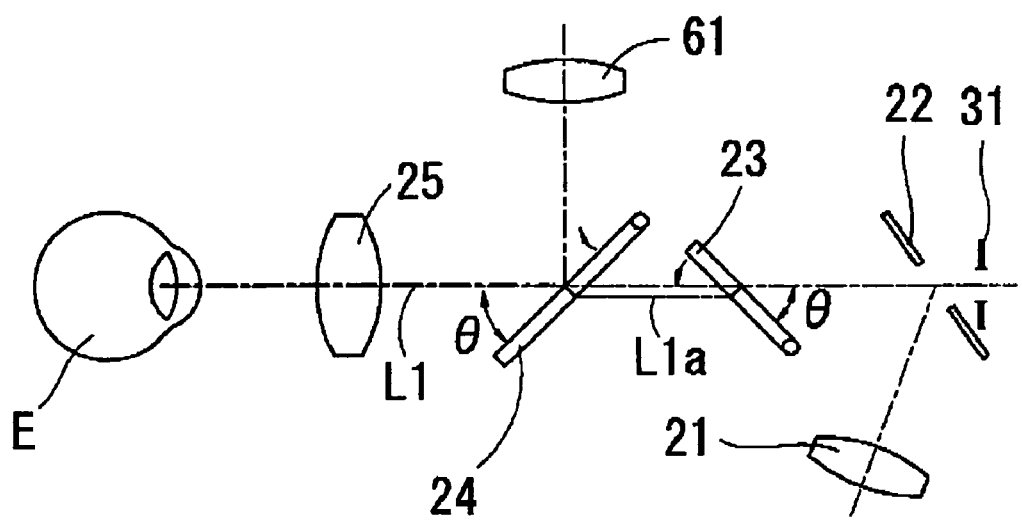
FIG. 3 is a view showing an occurrence of an optical axis deviation by insertion of an optical path dividing member, and correction thereof by insertion of a glass plate.

On an optical path between the objective lens 25 and the diaphragm 31 (the apertured mirror 22), a movable dichroic mirror 24 is arranged as an optical path dividing member. Further, on an optical path between the dichroic mirror 24 and the diaphragm 31 (the apertured mirror 22), a movable parallel glass plate 23 is arranged as a member for correcting an optical axis deviation caused by the dichroic mirror 24. The dichroic mirror 24 has a wavelength-selecting property of reflecting light within an infrared wavelength range of approximately 900 nm or more including light from an infrared illumination light source 58 for anterior-segment observation and that from the alignment target projection optical system 50 to be described later, and transmitting light within an infrared wavelength range of approximately 900 nm or less including light from the illumination optical system 10a for fundus observation and that from the focus target projection optical system 40 to be described later. The glass plate 23 has approximately the same thickness and refractive index as the dichroic mirror 24. Further, as shown in FIG. 3, the dichroic mirror 24 is arranged to have an angle of inclination of θ with respect to the optical axis L1, and the glass plate 23 is arranged to have an angle of inclination of 180° minus θ with respect to the optical axis L1. At the time of the fundus photographing, the dichroic mirror 24 and the glass plate 23 are flipped up synchronously by an inserting/removing mechanism part 66 and removed from the optical path. Besides, a known mechanism such as a solenoid and a cam (or a motor and the like) may be used for the inserting/removing mechanism part 66.

<Focus Target Projection Optical System 40>

Infrared target light emitted from an infrared light source 41 for focus target projection such as an infrared light-emitting diode passes through a slit target plate 42 and two deflection-angle prisms 43 attached to the target plate 42 and is reflected by the half mirror 44, and further passes through the relay lens 21 to the objective lens 25 to be projected onto the fundus Ef (i.e., the focus target is projected thereon). The light source 41 and the target plate 42 are moved in synchronization with the focusing lens 32 in the optical axis direction by the moving mechanism part 39. Incidentally, the light source 41 emits infrared light having a center wavelength of approximately 880 nm.

<Alignment Target Projection Optical System 50>

The alignment target projection optical system 50 includes a pair of first projection optical systems having optical axes arranged laterally symmetrical with respect to the optical axis L1, and a pair of second projection optical systems having optical axes arranged laterally symmetrical with respect to the optical axis L1 forming an angle smaller than the optical axes of the first projection optical systems. The first projection optical systems include infrared light sources 51 such as infrared light-emitting diodes which emit infrared light having a center wavelength of approximately 940 nm and collimating lenses 52, respectively, and project infrared target light at an infinite distance onto the eye E with approximately parallel light (i.e., alignment targets are projected thereon). On the other hand, the second projection optical systems include infrared light sources 53 such as infrared light-emitting diodes which emit infrared light having a center wavelength of approximately 940 nm, and project infrared target light at a finite distance onto the eye E with divergent light (i.e., alignment targets are projected thereon). Besides, the optical systems in FIG. 2 are viewed from the side. The alignment target projection optical system 50 is presented as if it is arranged vertically; however, it is actually arranged laterally.

<Anterior-segment Observation Optical System 60>

Infrared illumination light emitted from the infrared illumination light source 58 for anterior-segment observation such as an infrared light-emitting diode is reflected by an anterior-segment of the eye E and the dichroic mirror 24, passes through a field lens 61 and is reflected by a reflection mirror 62, further passes through an aperture of a diaphragm 63 and a relay lens 64, and is photo-received on a CCD camera 65 for anterior-segment observation having sensitivity to the infrared wavelength range to form an image of the anterior-segment of the eye E. Besides, the light source 58 emits infrared light having a center wavelength of approximately 940 nm. Further, the CCD camera 65 doubles as image-pickup means for alignment target detection (i.e., the anterior-segment observation optical system 60 doubles as an alignment target detection optical system), and picks up the image of the anterior-segment of the eye E formed by the light source 58 and images of the alignment targets formed by the alignment target projection optical system 50.

Incidentally, while it is advantageous to use alignment target detection means doubling as anterior-segment image pickup means as in the present embodiment, a dedicated one may be arranged.

<Fixation Target Presenting Optical System 70>

Red fixation target light emitted from a fixation target light source (a fixation lamp) 74 such as a red light-emitting diode passes through one of apertures in shielding plates 71 on a rotary disk 72 and a relay lens 75 to be transmitted through the dichroic mirror 37. A part of the red fixation target light transmitted through the dichroic mirror 37 is reflected by the dichroic mirror 34 and passes through the image forming lens 33 to the objective lens 25 to be projected onto the fundus Ef (i.e., a fixation target is projected thereon). The disk 72 is provided with eight shielding plates 71, and the aperture in each shielding plate 71 is either for guiding a visual line so that the vicinity of a posterior pole of the fundus of a right eye comes to a center of photographing, for guiding the visual line so that the vicinity of a posterior pole of the fundus of a left eye comes to the center of photographing, or for guiding the visual line so that a periphery of the fundus is photographed. The disk 72 is rotated by a pulse motor 73, and one of the eight shielding plates 71 is selectively arranged in front of the light source 74. Incidentally, the number of shielding plates 71 is not limited to eight.

Figure 7B:
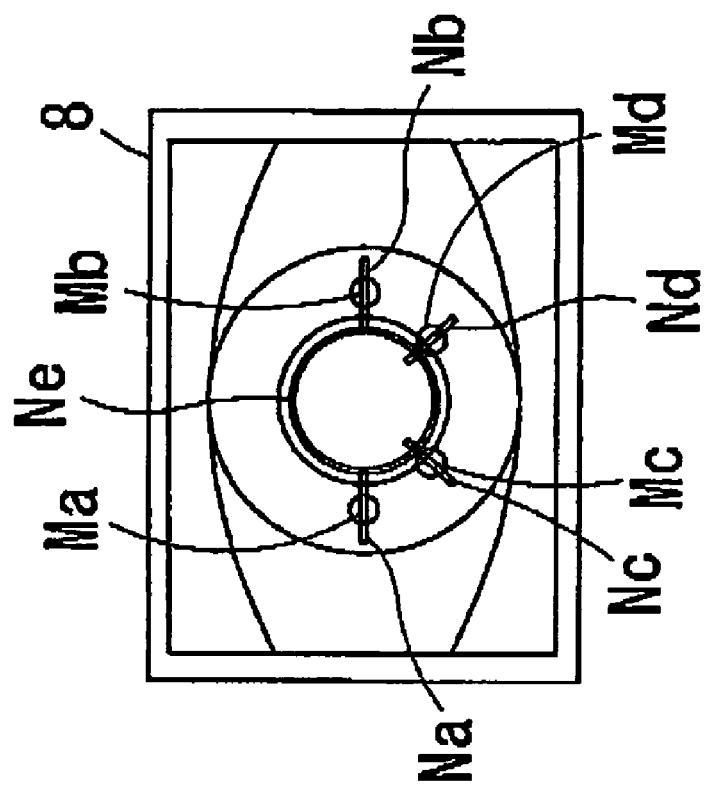
FIGS. 7A and 7B are views showing an example of an observation image of an anterior-segment of an eye.
Figure 7A:
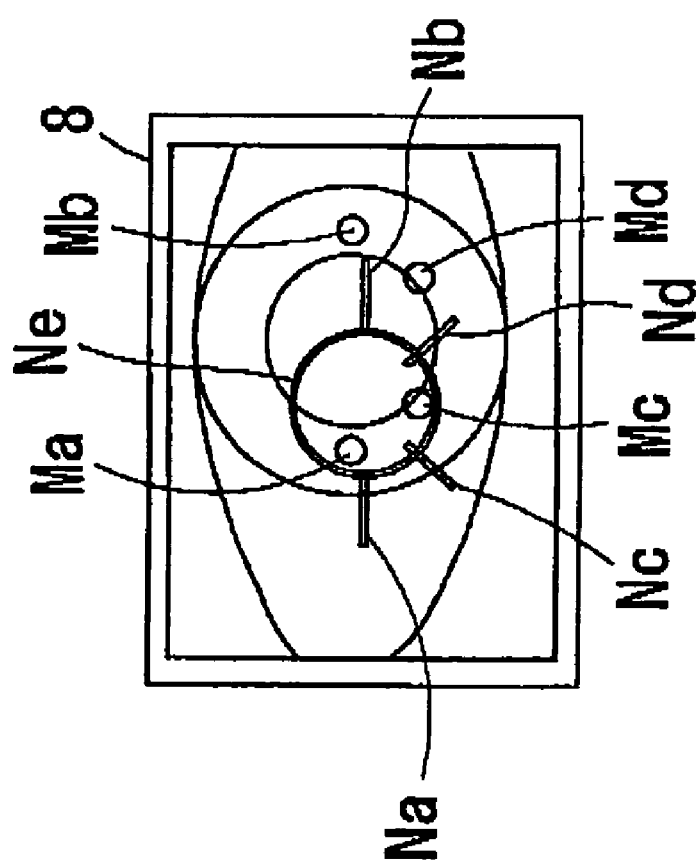

At the time of anterior-segment observation and alignment, the dichroic mirror 24 and the glass plate 23 are inserted into the optical path of the fundus observation/photographing optical system 30 (i.e., the optical path between the objective lens 25 and the diaphragm 31 (the apertured mirror 22)). The image of the anterior-segment formed by the light source 58 and the images of the alignment targets formed by the alignment target projection optical system 50 are reflected by the dichroic mirror 24 and picked up by the CCD camera 65. FIGS. 7A and 7B show the image of the anterior-segment and the images of the alignment targets picked up by the CCD camera 65 and displayed on the monitor 8. Target images Ma and Mb are the images of the alignment targets at an infinite distance formed by the first projection optical systems, and target images Mc and Md are the images of the alignment targets at a finite distance formed by the second projection optical systems. The second projection optical systems are arranged so that the target images Mc and Md are formed below the target images Ma and Mb.

Also at the time of the fundus observation and focusing, the dichroic mirror 24 and the glass plate 23 are inserted into the optical path of the fundus observation/photographing optical system 30. The image of the fundus Ef formed by the illumination optical system 10a for fundus observation and the image of the focus target formed by the focus target projection optical system 40 are transmitted through the dichroic mirror 24 and the glass plate 23 to be picked up by the CCD camera 38. At this time, as shown in FIG. 3, the optical axis L1 is deviated (shifted) to be an optical axis L1a by insertion of the dichroic mirror 24, and it is made back to the optical axis L1 by insertion of the glass plate 23. Therefore, the image of the anterior-segment and the image of the fundus Ef are favorably picked up by the CCD camera 65 and the CCD camera 38, respectively, at a time.

At the time of the fundus photographing, the dichroic mirror 24 and the glass plate 23 are removed from the optical path by the inserting/removing mechanism part 66. The image of the fundus Ef formed by the illumination optical system 10b for photographing is picked up by the CCD camera 35 via the objective lens 25 to the dichroic mirror 34.

Respective image signals outputted from the CCD cameras 65, 38 and 35 are inputted to an image processing part 80. The image processing part 80 detects the images of the alignment targets based on the image signal from the CCD camera 65 and the image of the focus target based on the image signal from the CCD camera 38. Further, the image processing part 80 is connected to the monitor 8 to control images displayed thereon. The control part 81 is connected with the image processing part 80, the Y-moving mechanism part 6, the X- and Z-moving mechanism part 7, the joystick 4, the inserting/removing mechanism part 27, the moving mechanism part 39, the inserting/removing mechanism part 66, the pulse motor 73, a photographing switch 83, a switch part 84 having various switches, the respective light sources, and the like. (In FIG. 2, a part of connecting lines are not illustrated.)

Figure 4:
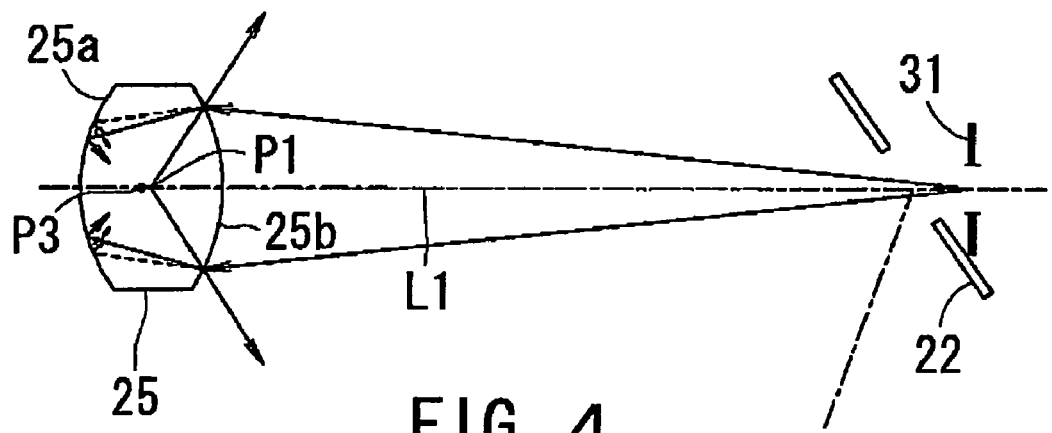
FIG. 4 is a view for illustrating arrangement positions of black-dot plates.
Figure 5:
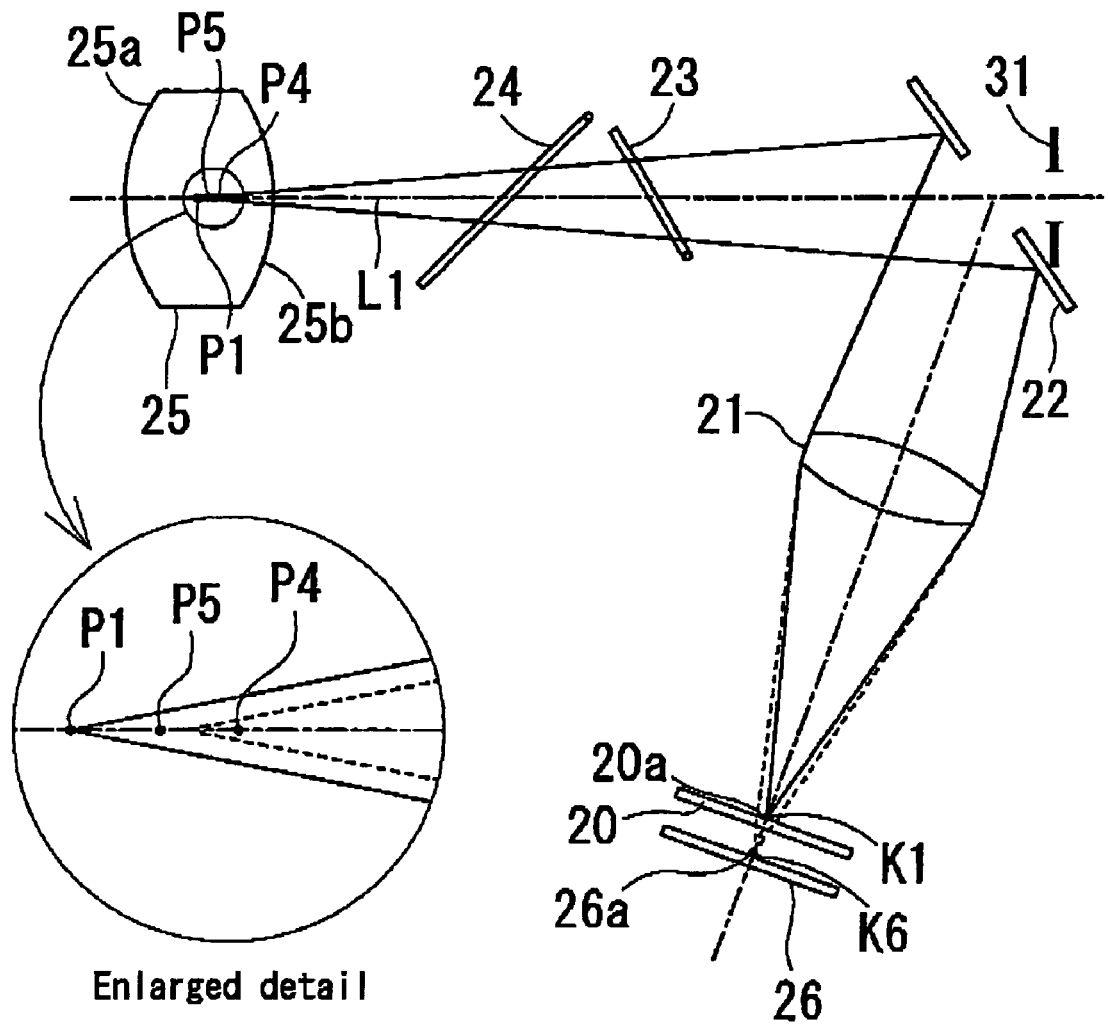
FIG. 5 is an another view for illustrating the arrangement positions of the black-dot plates.
Figure 6:
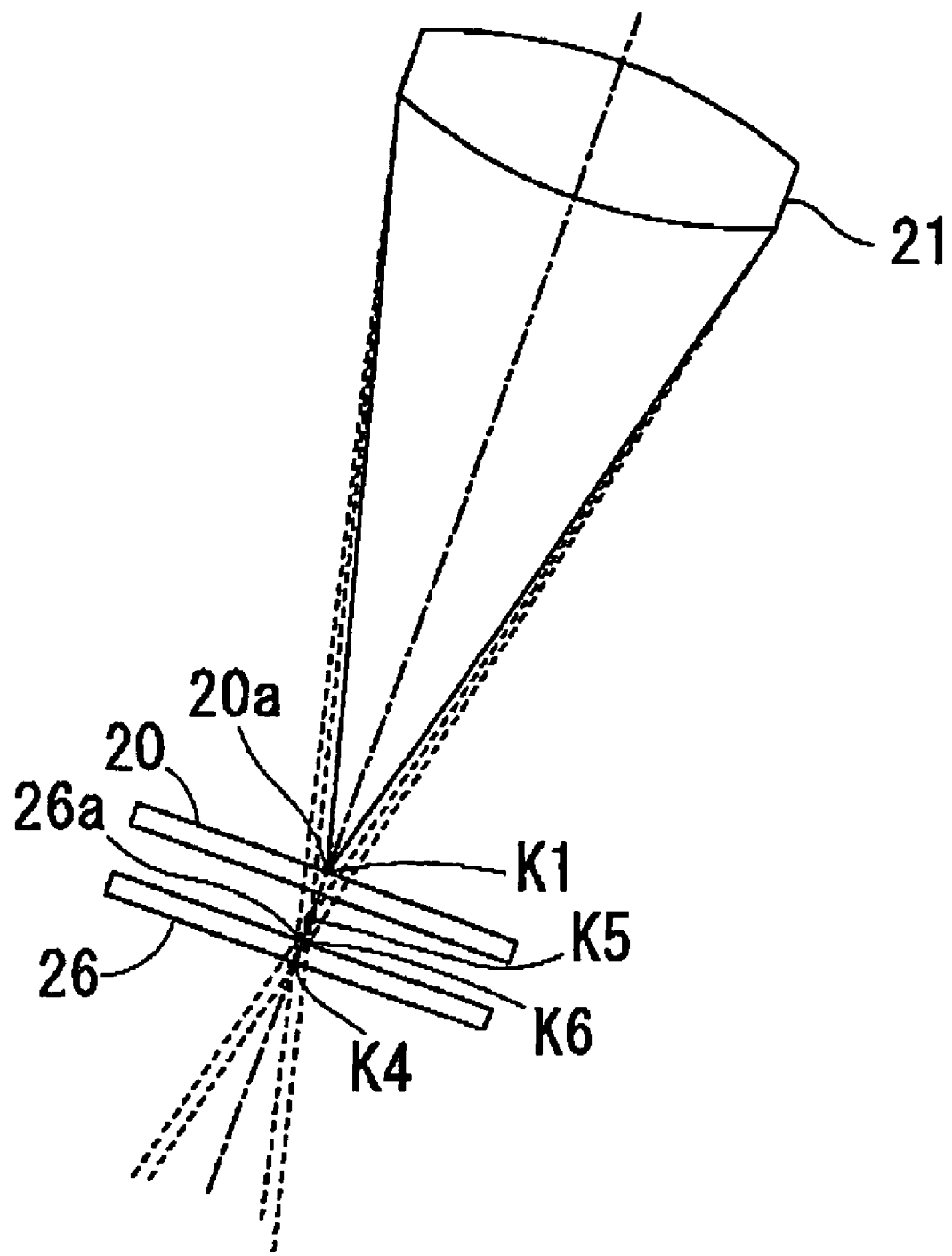
FIG. 6 is a still another view for illustrating the arrangement positions of the black-dot plates.

Next, the arrangement of the black-dot plate 20 and the black-dot plate 26 will be described with reference to FIGS. 4 to 6. As shown in FIG. 4, at the time of the fundus photographing in a state where the dichroic mirror 24 and the glass plate 23 are not inserted into the optical path between the objective lens 25 and the diaphragm 31 and when considering a case where the visible illumination light for photographing is reflected by a second surface (a surface facing the diaphragm 31) 25b of the objective lens 25, a conjugate point (position) with the aperture of the diaphragm 31 in relation to the second surface 25b (a point (position) at which a virtual image of the aperture of the diaphragm 31 is formed) is taken as a point P1. In addition, it is assumed that a first surface (a surface facing the eye E) 25a of the objective lens 25 is designed so that, when considering a case where the visible illumination light for photographing is transmitted through the second surface 25b and reflected by the first surface 25a, and is again transmitted through the second surface 25b, a conjugate point (position) with the aperture of the diaphragm 31 in relation to the first surface 25a (a point (position) at which a virtual image of the aperture of the diaphragm 31 is formed) coincide with the point P1. The black dot 20a in the black-dot plate 20 is, as shown in FIGS. 5 and 6, arranged at a point K1 representing a conjugate point (position) on the optical path of the illumination optical system 10 with the point P1 in relation to the second surface 25b and the first surface 25a. (Although FIG. 5 shows a state where the dichroic mirror 24 and the glass plate 23 are inserted into the optical path between the objective lens 25 and the diaphragm 31, this is to facilitate the comparison with a point (position) described later, and in regard to the relation between the point P1 and the point K1, a state where they are not inserted is shown). Further, the black dot 20a is made in such a size that its image covers at least the image of the aperture of the diaphragm 31, and is made as small as possible. This is because when the black dot 20a is made too large, an image of the black dot is apt to generate within the photographed image of the fundus Ef. In such a manner, the reflection light generated by the objective lens 25 (detrimental light) of the visible illumination light for photographing can be eliminated. Besides, for more details on the arrangement of the black dot 20a, see U.S. Pat. No. 4,098,549 corresponding to Japanese Patent Kokoku Publication No. Sho60-57852.

In the fundus camera of non-mydriasis type using the infrared illumination light for fundus observation, the reflection light generated by the objective lens 25 (detrimental light) of the infrared illumination light for fundus observation cannot be fully eliminated by using only the black dot 20a arranged for the visible illumination light for photographing. In other words, when using the infrared illumination light of which wavelength range is apart from the visible illumination light (having a center wavelength of 550 nm) (for example, the infrared illumination light having a wavelength of 880 nm), as shown in FIG. 4, the conjugate point (position) with the aperture of the diaphragm 31 in relation to the first surface 25a of the objective lens 25 is shifted to a point P3. On the other hand, the conjugate point (position) with the aperture of the diaphragm 31 in relation to the second surface 25b of the objective lens 25 remains at the point P1. Therefore, in order to cope with the deviation of the conjugate points (positions) with the aperture of the diaphragm 31 generated due to the difference in wavelengths, a black-dot plate (a black dot) for the infrared illumination light for fundus observation is provided aside from the black-dot plate 20 (the black dot 20a).

In this embodiment, description will be given on a case where the difference in wavelengths is considered. Besides, in this embodiment, since the dichroic mirror 24 and the glass plate 23 are inserted into the optical path between the objective lens 25 and the diaphragm 31 at the time of the fundus observation, an optical path length is changed relative to that at the time of the fundus photographing where the dichroic mirror 24 and the glass plate 23 are not inserted into the optical path between the objective lens 25 and the diaphragm 31. Therefore, the difference in optical path lengths is also considered. As shown in FIG. 5, at the time of the fundus observation in a state where the dichroic mirror 24 and the glass plate 23 are inserted into the optical path between the objective lens 25 and the diaphragm 31 and when considering a case where the infrared illumination light for fundus observation is reflected by the second surface 25b, the conjugate point (position) with the aperture of the diaphragm 31 in relation to the second surface 25b is taken as a point P4 (i.e., the point P1 is deviated to the point P4 due to the difference in optical path lengths). Additionally, when considering a case where the infrared illumination light for fundus observation is transmitted through the second surface 25b and reflected by the first surface 25a and is again reflected by the second surface 25b, the conjugate point (position) with the aperture of the diaphragm 31 in relation to the first surface 25a is taken as a point P5 (i.e., the point P3 is deviated to the point P5 due to the difference in optical path lengths). In FIG. 6, a point K4 represents a conjugate point (position) on the optical path of the illumination optical system 10 with the point P4 in relation to the second surface 25b, and a point K5 represents a conjugate point (position) on the optical path of the illumination optical system 10 with the point P5 in relation to the first surface 25a. The black dot 26a in the black-dot plate 26 is arranged at a point K6 between the point K4 and the point K5. The point K6 is preferably arranged at approximate the midpoint between the point K4 and the point K5 so as to efficiently cover the image of the aperture of the diaphragm 31. That is to say, on the part of the objective lens 25, as the image of the black dot 26a is formed at approximate the midpoint between the point P4 and the point P5, if the size thereof is arranged to cover the image of the aperture of the diaphragm 31, detrimental reflection light at the time of the fundus observation can be eliminated by using only the black dot 26a without excessively enlarging the black dot 26a. Incidentally, in the observation image of the fundus Ef, even if the image of the black dot 26a is generated largely in some degree, no problem is presented in observation and detection of the image of the focus target; therefore, the black dot 26a is not necessarily arranged at the point K6 and is preferably arranged thereabout in a size to cover the image of the aperture of the diaphragm 31. At the time of the fundus photographing, the black-dot plate 26 is removed from the optical path so that the image of the black dot 26a is not generated within the photographed image of the fundus Ef.

Operation at the time of the fundus photographing will be described. First, the face of the examinee is supported by the face support unit 5. In the early stage, the dichroic mirror 24 and the glass plate 23 are inserted into the optical path of the fundus observation/photographing optical system 30, and the image of the anterior-segment picked up by the CCD camera 65 is displayed on the monitor 8. While observing the image of the anterior-segment displayed on the monitor 8, the examiner moves the photographing part 3 in the X- and Y-directions so that the image of the anterior-segment is placed in the center of a screen on the monitor 8. In addition, the examiner moves the photographing part 3 in the Z-direction to bring the image of the anterior-segment into focus. When the image of the anterior-segment comes to be placed in the center of the screen on the monitor 8, as shown in FIG. 7A, the four target images Ma, Mb, Mc and Md also come to be displayed (appear) thereon. In FIG. 7A, reference letters Na, Nb, Nc and Nd indicate reticle marks respectively in a line shape, and a reference letter Ne indicates a ring mark for indicating a pupil diameter necessary for photographing, all of which are electrically formed by the image processing part 80. The alignment is made by moving the photographing part 3 in the X- and Y-directions so that the target images Ma, Mb, Mc and Md are respectively placed on the reticle marks Na, Nb, Nc and Nd as shown in FIG. 7B. Further, the photographing part 3 is moved in the Z-direction to bring the target images Ma to Md into focus.

Figure 8:
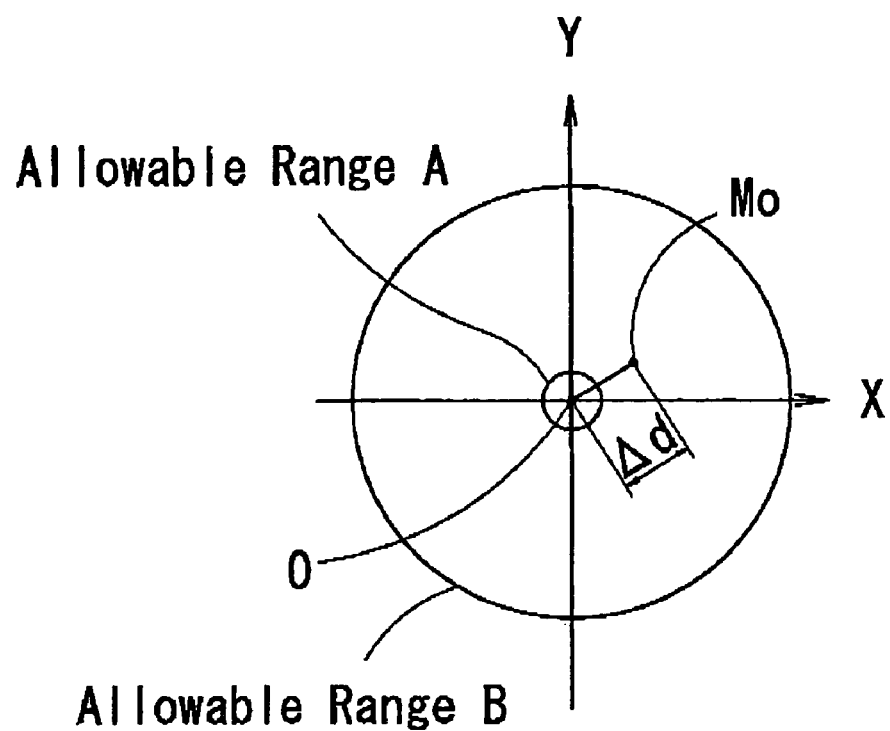
FIG. 8 is a view showing an example of a reference condition for alignment.

When the target images Ma to Md picked up by the CCD camera 65 are detected by the image processing part 80, the control part 81 obtains information on an alignment state in the X-, Y- and Z-directions based on the target images Ma to Md. That is to say, the control part 81 obtains, as shown in FIG. 8, a deviation (shift) amount Δd with respect to an alignment reference position O in the X- and Y-directions while defining the midpoint between the target images Ma and Mb as a corneal vertex position Mo. Then, the control part 81 judges appropriateness of the alignment state (i.e., alignment completion) in the X- and Y-directions based on whether the deviation amount Δd stably falls within a predetermined first allowable range A of alignment completion for a predetermined time (for example, 10 frames of image processing, 0.3 second, or the like) (i.e., whether a first reference condition A for alignment is satisfied). Further, the alignment state in the Z-direction is detected through comparison of a distance between the target images Ma and Mb to a distance between the target images Mc and Md. It utilizes a characteristic that in the case of forming corneal reflexes using light sources at an infinite distance and light sources at a finite distance, respectively, a height of corneal reflexes formed by the light sources at a finite distance is changed as a working distance is changed while a height of corneal reflexes formed by the light sources at an infinite distance is not changed even when the working distance is changed. (For more details, see U.S. Pat. No. 5,463,430 corresponding to Japanese Patent Application Unexamined Publication No. Hei6-46999.) The control part 81 obtains a deviation (shift) amount from an alignment reference position in the Z-direction, and judges appropriateness of the alignment state (i.e., alignment completion) in the Z-direction based on whether the deviation amount stably falls within a predetermined first allowable range of alignment completion for a predetermined time (i.e., whether a first reference condition for alignment is satisfied).

If the alignment state in the X-, Y- and Z-directions satisfies the first reference condition, display switching is made from the image of the anterior-segment to the image of the fundus Ef.

Figure 9:
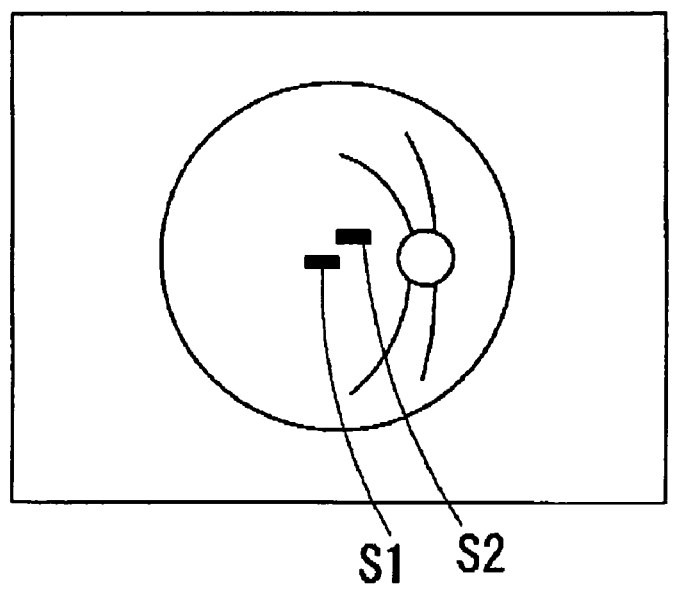
FIG. 9 is a view showing an example of an observation image of a fundus.

FIG. 9 shows an example of the screen when the display switching to the image of the fundus Ef is made. The examiner checks the focus of the image of the fundus Ef, a flare in the image of the fundus Ef and the like while observing the image of the fundus Ef, and performs further alignment so that the photographing may be performed in a desired state.

In the present fundus camera, even when the image of the fundus Ef is displayed on the monitor 8, the control part 81 obtains the information on the alignment state in the X-, Y- and Z-directions based on the image signal from the CCD camera 65 for the anterior-segment observation. Once the alignment is completed and the display switching is made from the image of the anterior-segment to the image of the fundus Ef, observation is made to know whether the deviation amount Δd in the X- and Y-directions falls within a predetermined second allowable range B of alignment which is set greater than the first allowable range A (i.e., whether a second reference condition B for alignment is satisfied). The second allowable range B is, for example, a range of +3-4 mm with respect to the alignment reference position O. If the deviation amount Δd goes beyond the second allowable range B, the infrared illumination light becomes difficult to reach the fundus Ef, so that the image of the fundus Ef tends to be unobservable. Similarly, for the Z-direction, observation is made to know whether the deviation amount falls within a predetermined second allowable range of alignment which is set greater than the first allowable range for alignment completion (i.e., whether a second reference condition for alignment is satisfied). Further, when the alignment state (deviation amount) in either of the X-, Y- and Z-directions comes not to satisfy the second reference condition (second allowable range), the display switching is automatically made from the image of the fundus Ef to the image of the anterior-segment.

After the alignment while the image of the fundus Ef is observed, as shown in FIG. 9, focus target images S1 and S2 formed by the focus target projection optical system 40 are displayed (appear) in the center. Therefore, the light source 41, the target plate 42, and the focusing lens 32 are moved in the optical axis direction based on the target images S1 and S2 for performing focusing on the fundus Ef. If the fundus Ef is out of focus, the target images S1 and S2 are displayed (appear) separately, and if the fundus Ef is in focus, they are displayed (appear) in coincident with each other. Incidentally, at this time, since the black-dot plate 26 is inserted into the optical path, the reflection light generated by the objective lens 25 (detrimental light) does not pass through the aperture of the diaphragm 31; therefore, the target images S1 and S2 can be fully recognized and the focusing on the fundus Ef can be easily performed.

While the focusing can be performed manually, the present apparatus is provided with an automatic focusing mechanism. The target images S1 and S2 are detected and processed by the image processing part 80, and their separation information is transferred to the control part 81. Based on the separation information on the target images S1 and S2, the control part 81 drives and controls the moving mechanism part 39 so that both of the images coincide with each other to perform focusing on the fundus Ef. Upon completion of the focusing, the examiner presses the photographing switch 83 to implement the photographing. In the case of automatic focusing, it is specially effective to suppress the generation of detrimental light due to the reflection by the objective lens 25 through the insertion of the black-dot plate 26 because the target images S1 and S2 become detectable.

When a trigger signal from the switch 83 is inputted, the control part 81 drives and controls the inserting/removing mechanism part 66 to remove the dichroic mirror 24 and the glass plate 23 from the optical path, and drives and controls the inserting/removing mechanism part 27 to remove the black-dot plate 26 from the optical path, to have the light source 14 emit light. Through the emission from the light source 14, the fundus Ef is illuminated with the visible light, and the reflection light from the fundus Ef is photo-received on the CCD camera 35 to form the image of the fundus Ef. Then, on the monitor 8, the image of the fundus Ef picked up by the CCD camera 35 is displayed in colors. In addition, the image of the fundus Ef (photographed image) is stored in an image memory in the image processing part 80.

Figure 10:
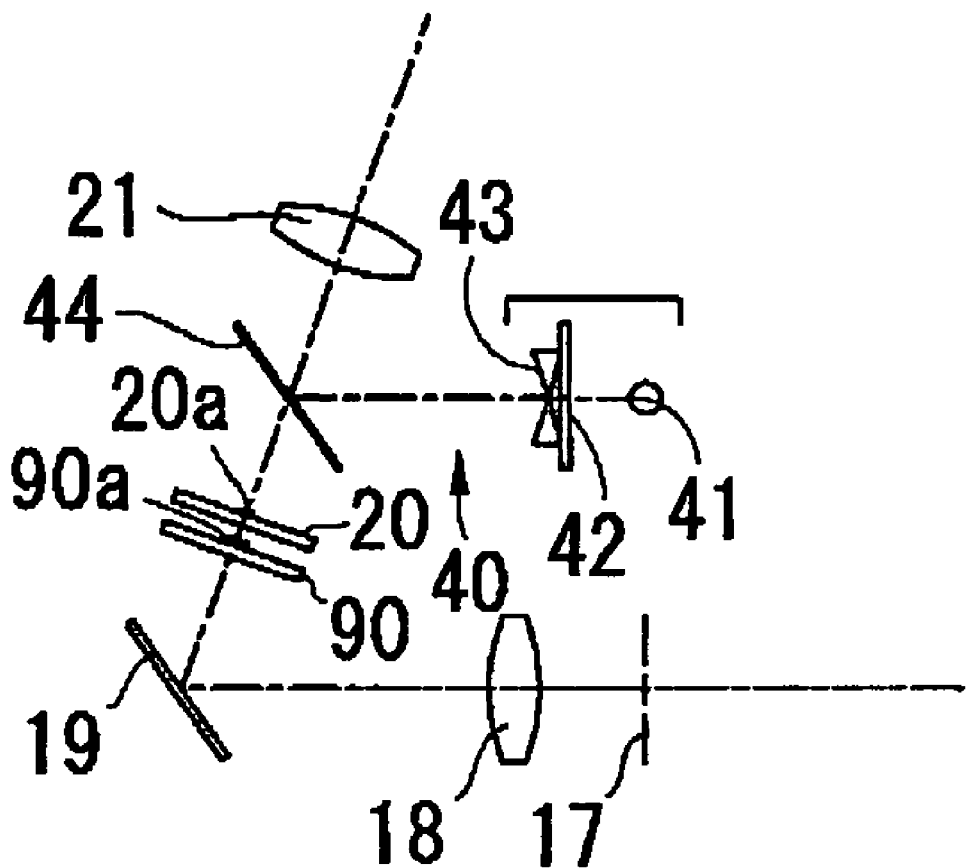
FIG. 10 is a view showing a modified example of the preferred embodiment consistent with the present invention.

In the above description, the mechanism for inserting/removing the black-dot plate 26 for the infrared illumination light for fundus observation into/from the optical path of the illumination optical system 10 is used; however, a modified example as shown in FIG. 10 may be employed. The same members as in the previous example are assigned the same reference numerals, and the constituting members not shown in FIG. 10 are the same and omitted from illustration. A black dot 90a at the center of a black-dot plate 90 in the modified example is formed by a coating having a property of shielding the infrared illumination light for fundus observation and transmitting the visible illumination light for photographing. The arrangement position and size of the black dot 90a are the same as in the previous example. In the modified example, since the visible illumination light for photographing is transmitted without shielded by the black dot 90a, the mechanism for inserting/removing the black-dot plate 90 can be omitted in contrast to the previous example. Besides, another configuration may be employed where the glass plate constituting the black-dot plate 20 for the visible illumination light for photographing is used in common, and the black dot 20a is provided on the surface facing the lens 21 and the black dot 90a having a property of shielding the infrared light and transmitting the visible light is formed on the other surface, without the need for providing the dedicated black-dot plate 90. In such a case, the constituting members can be further simplified. Though the thickness of the glass plate constituting the black-dot plate 20 is preferably set in consideration of the arrangement position of the black dot 90a, it is essential only that the black dot 90a is at a position easy to arrange and in such a size that detrimental reflection light can be eliminated because little problems are presented even if the image of the black dot 90a is somewhat observed in the observation image of the fundus Ef.

Incidentally, the arrangement position and size of the black dot 26a shown in FIG. 6 (the black dot 90a shown in FIG. 10) consistent with the embodiment described above are determined in association with the difference in wavelengths between the illumination light and the difference in optical path lengths so that the black dot 26a is arranged in the vicinity of the conjugate position with the aperture of the diaphragm 31 and the infrared illumination light for fundus observation reflected by the objective lens 25 does not pass through the diaphragm 31, while they are also determined in consideration of the following matters. That is to say, a refractive index differs between the visible light and the infrared light in relation to a lens system (the lens 21) arranged between the objective lens 25 and the black-dot plate 20 in the common optical path among the illumination optical system 10a for fundus observation and the illumination optical system 10b for photographing (the difference in color aberrations exists in relation to the lens 21). Therefore, the conjugate position with the aperture of the diaphragm 31 in connection with the infrared illumination light for fundus observation is deviated toward the light source 11 with respect to the position of the black dot 20a. Accordingly, the position of the black dot 26a (90a) is preferably determined by a calculation in consideration of the amount of the difference in color aberrations in relation to the lens system arranged between the objective lens 25 and the black-dot plate 20.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye of an examinee, the fundus camera comprising:
   a photographing/observation optical system having an objective lens and a diaphragm arranged at a conjugate position with a pupil of the eye in relation to the objective lens, for performing visible photographing and infrared observation of the fundus via the objective lens and an aperture of the diaphragm;
   an illumination optical system for illuminating the fundus with visible light for photographing and infrared light for observation via the objective lens;
   a first black-dot plate provided with a first black dot that is in a size to cover an image of the aperture of the diaphragm and arranged at a position on an optical path of the illumination optical system, the position conjugate with a position at which a virtual image of the aperture of the diaphragm is formed in relation to a reflection surface in a case where the visible light for photographing is reflected by the objective lens; and
   a second black-dot plate provided with a second black dot that is in a size to cover an image of the aperture of the diaphragm and arranged in the vicinity of a position on the optical path of the illumination optical system, the position conjugate with a position at which a virtual image of the aperture of the diaphragm is formed in relation to the reflection surface in a case where the infrared light for observation is reflected by the objective lens, wherein
   the first black dot is arranged to be fixed on the optical path and shields at least the visible light for photographing,
   the second black dot is arranged to be removable on the optical path and shields the visible light for photographing and the infrared light for observation, and
   the second black dot is removed from the optical path at the time of the visible photographing and is inserted into the optical path at the time of the infrared observation.

2. A fundus camera for photographing a fundus of an eye of an examinee, the fundus camera comprising:
- a photographing/observation optical system having an objective lens and a diaphragm arranged at a conjugate position with a pupil of the eye in relation to the objective lens, for performing visible photographing and infrared observation of the fundus via the objective lens and an aperture of the diaphragm;
- an illumination optical system for illuminating the fundus with visible light for photographing and infrared light for observation via the objective lens;
- a first black-dot plate made of a glass plate and provided with a first black dot at its center that is in a size to cover an image of the aperture of the diaphragm which is arranged at a position on an optical path of the illumination optical system, the position conjugate with a position at which a virtual image of the aperture of the diaphragm is formed in relation to a reflection surface in a case where the visible light for photographing is reflected by the objective lens; and
- a second black-dot plate made of a glass plate and provided with a second black dot at its center that is in a size to cover an image of the aperture of the diaphragms which is arranged in the vicinity of a position on the optical path of the illumination optical system, the position conjugate with a position at which a virtual image of the aperture of the diaphragm is formed in relation to the reflection surface in a case where the infrared light for observation is reflected by the objective lens, wherein
- the first black-dot plate is arranged to be fixed on the optical path and the first black-dot shields at least the visible light for photographing and
- the second black-dot plate is arranged to be fixed on the optical path, and the second black-dot is formed by a coating having a property of transmitting the visible light for photographing and shielding the infrared light for observation.

* * * * *